United States Patent
Pompei, Jr.

[11] Patent Number: 6,140,549
[45] Date of Patent: Oct. 31, 2000

[54] BANDAGE HANDY STRIPS

[76] Inventor: John Anthony Pompei, Jr., 63 Yarde Dr., Forestville, Conn. 06010

[21] Appl. No.: 09/229,641

[22] Filed: Jan. 13, 1999

[51] Int. Cl.$^7$ .............................. A61F 13/00; A61B 17/06
[52] U.S. Cl. ................................. 602/57; 602/41; 602/43; 602/54; 206/440; 206/441
[58] Field of Search .................................... 206/440, 441; 602/41–59; 128/888, 889; 221/312 C, 33, 209

[56] References Cited

U.S. PATENT DOCUMENTS

| | | | |
|---|---|---|---|
| 2,880,863 | 7/1959 | Stanton | 206/441 |
| 2,889,039 | 6/1959 | Schladermundt et al. | 206/441 |
| 2,897,961 | 8/1959 | Bush | 206/441 |
| 2,924,331 | 2/1960 | Hoey | 206/441 |
| 2,927,669 | 3/1960 | Look, Jr. | 206/441 |
| 2,965,223 | 12/1960 | Schladermundt et al. | 206/441 |
| 2,969,145 | 1/1961 | Hannauer, Jr. | 206/441 |
| 3,530,494 | 9/1970 | Baratta | 206/441 |
| 4,194,624 | 3/1980 | Spiegelberg | 206/441 |
| 5,000,172 | 3/1991 | Ward | 128/888 X |
| 5,099,832 | 3/1992 | Ward | 602/57 |
| 5,333,753 | 8/1994 | Etheredge | 221/33 |
| 5,336,162 | 8/1994 | Ota et al. | 602/41 |
| 5,533,962 | 7/1996 | Peterman et al. | 602/54 |
| 5,628,724 | 5/1997 | DeBusk et al. | 602/58 |
| 5,685,833 | 11/1997 | Turngren | 602/58 |

*Primary Examiner*—Kim M. Lee
*Attorney, Agent, or Firm*—Patent & Trademark Services; Thomas Zack; Joseph H. McGlynn

[57] ABSTRACT

A layered mounting for removably retaining a bandage between two facing wrapping sheets. An inner wrapping sheet with adhesive edges is fixed to a backing board while the edges of an outer wrapping sheet engage the adhesive edges of the inner sheet. Between the two facing wrapping sheets are an application tab and a bandage. The application tab have a lower portion retained to the inner wrapping sheet and an upper removal portion with an opposite end tab. These application tab fit over and cover a conventional bandage having a center fluid absorbing pad and two adhesive adjacent side surfaces. A pull tab on the outer wrapper sheet when pulled is used to expose the retained application tab and bandage. The upper portion of the application tab and the bandage can be removed from the two wrappers and the bandage applied to the wound area skin of a user. After doing so, the upper portion of the application tab is discarded. Two or more sets of inner and outer wrappers each with their own separate retained application tab and bandages contents may be used on a single backing board with different sized bandages in each separate set. The backing board may be adhesively retained on a flat surface such as the vertical back non-mirrored side of a medicine cabinet door to permit the one hand application of a removed bandage to a wound.

5 Claims, 2 Drawing Sheets

BANDAGE HANDY STRIPS

BACKGROUND OF THE INVENTION

Anyone who has ever been cut and is in need of a bandage knows that locating a bandage and then applying the bandage to the, cut is not always an easy chore. When the cut is on one hand and no help is available, the user must struggle with first locating the bandage, then removing its sterile wrapping and then with the other uncut hand applying the bandage.

The present invention is directed to a bandage mount that can be conveniently mounted on a flat surface, such as the reverse side of the door of a medicine cabinet, wherein a user with one hand may remove the sterile bandage from the mount and apply it directly to ones person all as detailed hereafter.

DESCRIPTION OF THE PRIOR ART

Bandages composed of different material are known. For example, in the Ota et al. invention (U.S. Pat. No. 5,336,162) the medical bandage has a substrate, a support of butted two pieces of plastic film having at least one extension part beyond the end of the substrate, and a releasable strip of plastic adhesive tape stuck to the butting part with non-adhesive side parts.

The Peterman et al. patent (U.S. Pat. No. 5,533,962) discloses a ringless adhesive bandage with a peripherally raised non-adhesive thin layer bordering the adhesive surface.

In U.S. Pat. No. 5,628,724 to DeBusk et a . the wound dressing and delivery system disclosed having a membrane film wound dressing, a relatively stiff substantially planar carrier sheet with tabs, and a releasable cover.

In the Turngren reference (U.S. Pat. No. 5,685,833) there is disclosed a bandage encapsulated in a protective sterile covering allowing the bandage to be removed from the sterile covering and applied with one hand without contaminating any portion of the bandage.

The present invention relates to a bandage mount having a covered bandage layered under a bandage wrapper and application tab all as more fully set forth in this specification.

SUMMARY OF THE INVENTION

This invention relates to a bandage mount that can adhesively be affixed to a flat surface having an inner bandage wrapper layer fixed to the mount and an outer bandage wrapper layer. Between the inner and outer wrapper layer sheets are application tab used to retain and cover a bandage that is to be applied to a wound.

It is the primary object of the present invention to provide for an improved mount for an easily accessible covered bandage that can be applied to a wound using one hand .

Another object is to provide for such a mount wherein the mount has an adhesive backing for mounting on a flat surface and a facing layer with an outwardly facing surface on which is mounted a bandage with an outer sterile wrapper which is peeled away from the bandage by means of pull tabs allowing one hand application of the bandage to a wound.

These and other objects and advantages of the present invention will become apparent to readers from a consideration of the ensuing description and the accompanying drawings.

DESCRIPTION OF THE PREFERRED EMBODIMENT

Figure 1:
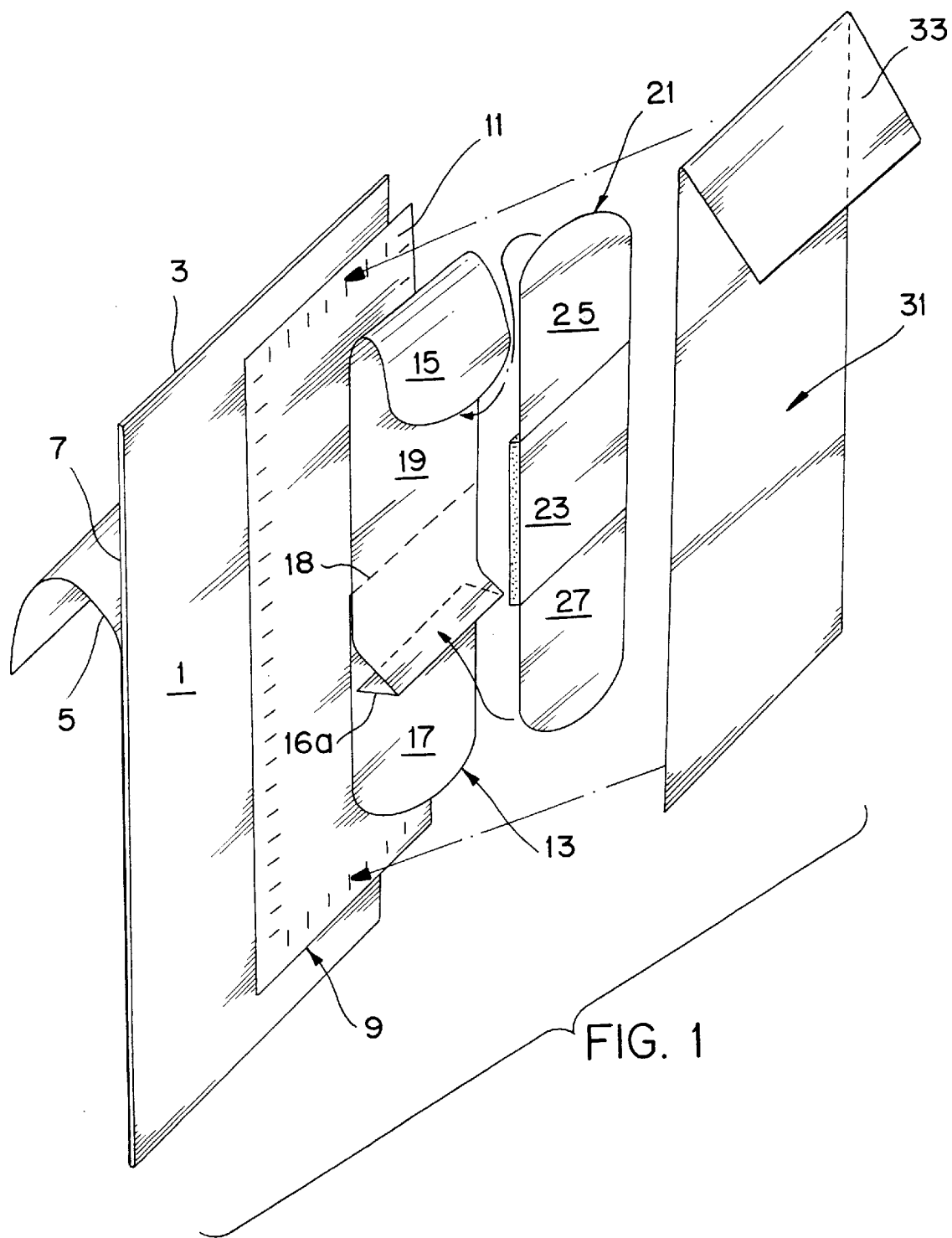
FIG. 1 is a perspective front view of the invention's preferred embodiment.

FIG. 1 is a perspective front view of the invention's preferred embodiment. The large surface area mounting backing board I has a uniform thickness 3 and is generally shaped as a rectangular planar surface. Extending substantially across the entire back surface area is a peelable sheet 5 that is held to the board's facing surface by a non-setting adhesive material 7 or the back surface of board 1. By peeling the sheet 5 off the back of board 1, the adhesive layer is exposed and the board may be bonded to any convenient flat surface such as, the vertical back non-mirrored side of a medicine cabinet's door.

On the front side of the board 1 fixedly secured thereto is the bandage back wrapper sheet 9 with its peelable adhesive peripheral front edge surface 11. Facing against the adhesive part of sheet 9 is the back surface of the application tab 13. The application tab 13 has a single upper sect on made up of a pull tab portion 15, and an intermediate portion 19 with its lower tab portion 16. Under tab portion 16 is a folded end extension tab 16a that also extends over lower tab 17. This folded free folded and extension tab 16a acts as an additional tab to permit the easy removal of application tab portions 15, 16 and 19 from the bandage once the bandage has been stuck to the wound by bandage portion 27. Thus, as the bandage is peeled away from the wrapper using tab 15, the exposed bandage portion 27 is applied near to the wound area. The user then grasps extension tab 16a and pulls the entire application tab away while the bandage is pulled over the wound.

Portions 16 and 16a overlaps the underlining lower tab 17 and is peelable away from wrapper sheet 9 while tab 17 remains fixed to wrapper sheet 9. Lower tab 17 extends to its defining upper end line 18 which runs across the width of application tab 13. Tab 17 is separate from the tab 16 and 16a, the portion 19 and the upper pull tab 15. The larger area and lower back tab portion 17 Was a total surface area that is partially overlapped by the smaller front intermediate portion 19 area. The upper pull tab 15 serves as a handle to remove a bandage and the upper portion of the application tab 19, as will be apparent in the following discussion, and along with its lower tab 16 also serves to keep a mounted bandage covered until removed after being applied by a user. The lower portion of application tab 13, defined as that portion of the application tab under portion 19 extending to line 18, remains fixed to the back wrapper sheet 9 during this bandage removal process.

The conventional bandage 21 has a fluid absorbing center pad section 23 with an adjacent adhesive upper sector 25 and an a ajacent adhesive lower sector surface 27 with one adhesive sector being on opposite sides of the center pad. The outer backing surface of the bandage 21 that does not engage) a user's skin, faces away from the application tab 13 and is made of a non-adhesive outer protective surface such as a plastic or vinyl covering. The bandage's two tipper and lower adhesive front sectors 25 and 27 face toward the application tab 13 with the upper adhesive sector 25 adhering to the upper part of portion 19 with upper tab 15 overlapping the non-adhesive backing of sector 25. When in place on the application tab, the bandages absorbent center pad section 23 is covered by the tab 16 without any adhesive contact and the lower adhesive sector 27 direct y adheres to the lower tab 17

Completely covering the surface area of he bandage 21 and the application tab 13 is the larger area front bandage wrapper sheet 31. Forming part of the front bandage wrapper is the upper bent portion 33 which is used as a pull tab for removing the sheet 31. The inner facing peripheral edges of the sheet 31 engage the adhesive peripheral edges 11 on the back wrapper 9 to sandwich and retain the bandage 21 along with the application tab 13 between the two larger surface area sheets made up of the bandage wrapper sheets 9 and 31.

The outer wrapper sheet 31 thus acts as a protective outer sheet that may be peeled away from its adhesive held back wrapper sheet 9 to allow a user with one hand to pull the then revealed bandage covering tab 15 to release the mounted application tab upper portion and bandage 21 from the retained lower portion of the application tab 13.

The facing surface areas of the outer bandage wrapper sheet 31 and the inner or back bandage wrapper sheet 9 are substantially the same and each are individually larger than the facing surface areas of either the application tab 13 or the bandage 21. Except for the added area made up by upper tab 15, the surface areas for the bandage 21 and the application tab 13 are the same.

Figure 2:
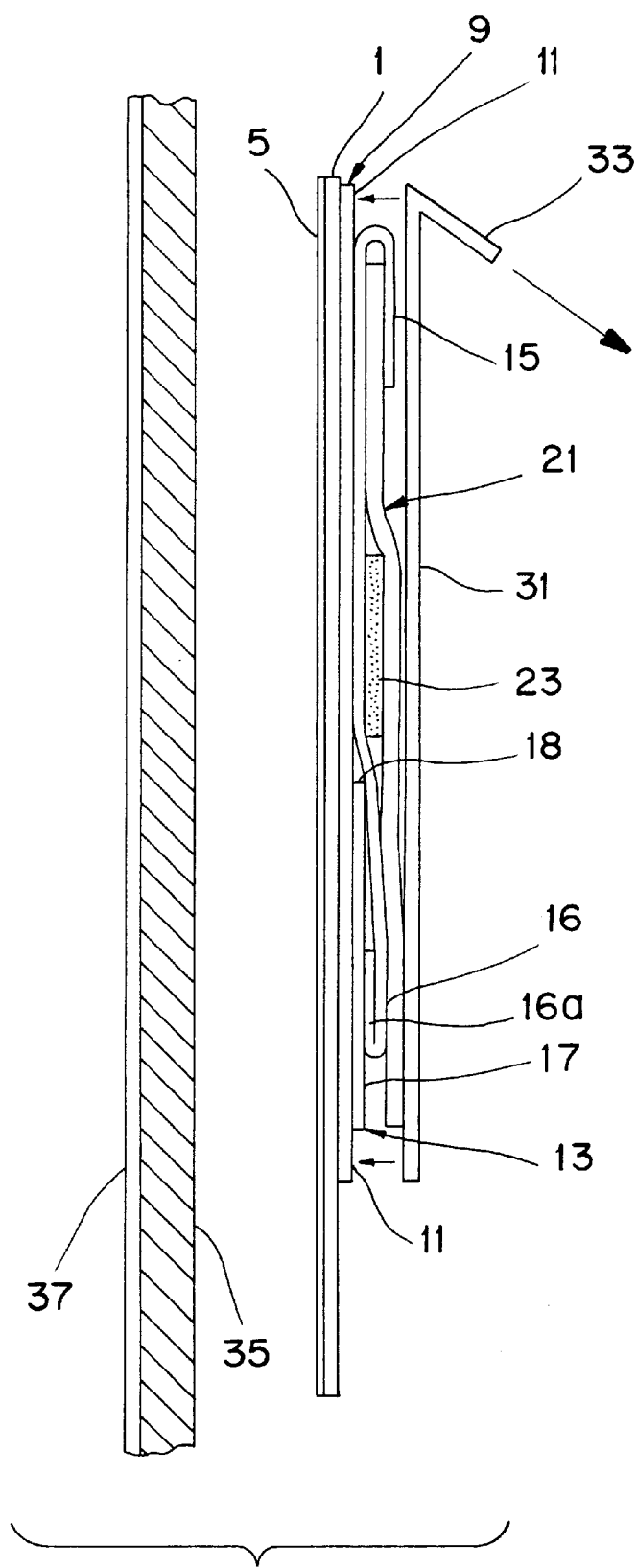
FIG. 2 is a side view of the different layer of the FIG.1 preferred embodiment when flush with each other.

FIG. 2 is a side view of the different layers of the FIG.1 preferred embodiment when each layer is adjacent its facing layer. In this second figure the peelable sheet 5 is shown flush against the back of board 1 and adhesively held to it. Once, this disposal backing sheet 5 is removed, the facing adhesive surface layer 7 on the back of board 1 is exposed such that the board 1 may be placed against and held to any convenient flat surface, such at the shown vertical surface of a medicine cabinet door 35 (shown in cross section) that is located on the side opposite the cabinet's front mirrored side 37. The bandage back wrapper sheet 9 is somewhat smaller in surface area than the surface area of the board 1 and is positioned flush against it.

An interposed bonding material may be used to fixedly secure the two abutting facing layers of the board 1 and sheet 9 together. On the opposite side of sheet 9 along its front facing peripheral edges are the non-setting adhesive edges 11 which extend around the sheet on all sides. The edges 11 permit the joined facing outer edges of outer wrapper sheet 31, when joined thereto, to be peeled away from the sheet 9 when exposure of the intervening retained contents is desired. The small arrows on the upper and lower inner edges of cuter wrapping sheet 31 indicate the direction this sheet must go to join with the inner wrapper sheet 9 along their mating edges. Sandwiched between the inner and outer wrapper sheets 9 and 31, respectively, are the application tab 13 and the retained conventional bandage 21. The bandage separated adhesive layers 25 and 27 are completely covered by both the application tab and the larger area outer wrapper sheet 31 to protect the bandage's sterile condition.

The material selected for the tab 13 is such that it does not permanently adhere to the bandage's adhesive sectors or portions contacted. The upper application tab 15 overlaps the top surface of the seated bandage. The lower application tab portion 17 remains fixed to the inner wrapper sheet 9 while the upper removal overlapping portion of the application tab 13 that retains the bandage and has end tabs 15 and 16 remains covering the bandage.

When it is desired to expose the seated bandage 21 and apply it to a wound, the outer wrapper is first removed from the sheet 9 by pulling down on its upper tab 33 and then discarded. This action exposes the bandage 21. Since the bandage's lower adhesive sector 27 is temporarily fixed to the application tab lower tab 17, it does initially not fall away from the inner wrapping sheet 9 when the outer wrapping sheet is removed. To remove the bandage from the application tab, the tab 15 is pulled. This removes the entire bandage leaving its pad 23 and upper adhesive sector 25 still covered by the protective application tab portions 16 and 19 while the bandage's lower adhesive sector 27 is exposed thereby permitting the application of the bandage to the wound area. Once the bandage's lower sector 27 is adhered around the wound area, the remainder of the bandage—pad 23 and upper adhesive sector 25—can be properly applied over the entire wound area by peeling away the application tab portions 15, 16 and 19 using the tab portion 16a. During this one hand bandage application process, sterility is maintained by holding the tab 15 with one's fingers.

If desired, more than one set of separate facing sheets 9 and 31 with their sandwiched internal contents, application tab find bandage contents, may be applied to a given single much larger backing board 1 sized to fit all such separate sheets. If desired, in this arrangement different sized bandages may be located on the same backing board 1 thereby insuring the user can have access to a greater variety of different sized bandages for use when needed. Other variations are also possible, for example, the board 1 and the two inner and outer wrapper sheets need not be flat planar sheets but could be bendable or deformable sheets shaped to fit flush against and on a greater variety of backing supporting surfaces such as irregular surfaced paneled cabinet doors, under sinks, etc.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A layered mounting for removably retaining a bandage, comprising:

a backing board having an inner wrapper sheet affixed to its front surface, said inner wrapper sheet having outer adhesive peripheral edges;

a backing sheet peelable from and adhesively held to a back surface of said backing board, said backing sheet when removed from said back surface providing an exposed adhesive surface on the backing board to permit the attachment of the board to a supporting surface;

a bandage;

applications tab the bandage, said applications tab having a lower portion fixed to said inner wrapper sheet and a separate upper removal portion having end tabs, said bandage being mounted between the end tab of the application tabs wherein the end tabs substantially engage the entire surface area of the bandage; and an outer wrapper sheet mounted to the inner wrapper sheet along the inner wrapper sheet's adhesive peripheral edges to retain the applications tabs and bandage between said inner and outer wrapper sheets.

2. The layered mounting as claimed in claim 1, wherein one of said end tabs for said applications tab is an upper pullable tab used to remove the upper portion of the applications tab and bandage away from the lower portion of the application tab fixed to said inner wrapper sheet.

3. The layered mounting a claimed claim 2, wherein said outer wrapper sheet is a sheet with and extending upper tab used to pull the outer wrapper sheet away from said inner wrapper sheet.

4. The layered mounting as claimed in claim 3, wherein the separate upper removal portion of said applications tab has an upper pull tab used to pull the upper portion and its engaged bandage away from the lower applications tab portion which is retained on said inner wrapper sheet.

5. The layered mounting as claimed in claim 4, wherein said bandage has a center fluid absorbing pad with an upper adhesive sector surface and a lower adhesive sector surface, said upper and lower adhesive sector surfaces facing towards said applications tabs.

\* \* \* \* \*